United States Patent [19]
Joslin

[11] Patent Number: 6,102,877
[45] Date of Patent: Aug. 15, 2000

[54] ARM SLING

[75] Inventor: Marianne Joslin, Brisbane, Calif.

[73] Assignee: Fancastic Products, Inc., Brisbane, Calif.

[21] Appl. No.: 09/388,992

[22] Filed: Sep. 2, 1999

Related U.S. Application Data

[60] Division of application No. 09/129,197, Jul. 23, 1998, which is a continuation-in-part of application No. 08/665,271, Jun. 17, 1996, Pat. No. 5,792,083.

[51] Int. Cl.⁷ .............................. A61F 5/00; A61F 13/00
[52] U.S. Cl. ................................................. 602/4; 602/62
[58] Field of Search ............................... 602/4, 5, 20–22, 602/60–62, 75–77; 128/878–880

[56] References Cited

U.S. PATENT DOCUMENTS

| | | | |
|---|---|---|---|
| 2,539,677 | 1/1951 | Teare | 602/4 |
| 2,935,066 | 5/1960 | Holloway | 602/21 |
| 3,371,663 | 3/1968 | Apgar | 602/4 |
| 4,622,961 | 11/1986 | Christensen | 602/4 |
| 5,086,762 | 2/1992 | Chee | 602/4 |
| 5,334,132 | 8/1994 | Burkhead | 602/4 |
| 5,792,083 | 8/1998 | Joslin | 602/5 X |

*Primary Examiner*—John Mulcahy
*Assistant Examiner*—Denise Pothier
*Attorney, Agent, or Firm*—Townsend and Townsend and Crew

[57] ABSTRACT

A longitudinally symmetric arm sling for supporting a forearm of a person has first and second substantially identical panel sections, made of one piece or sewn together from two panel halves so that the sections define a trough with a closed aft end and an open front end into which the arm can be placed. A strap has a first end attached to the aft end of the panel sections and a second end attached to the front end of the panel sections so that portions of the strap and of the panel sections adjacent the front end define opposing loops into which a thumb or the four fingers of a patient's hand can be extended irrespective of whether the sling is worn on a right arm or a left arm. The strip is relatively wide and sewn to the panel sections so that wide sides of the strip are parallel to the panel sections. The sling and the strap are constructed of a relatively soft, stretchable material. The effective length of the sling is less than the arm of the patient so that, when the sling is applied to the arm and the hand engages a loop of the sling at the front end thereof, the sling must be stretched to accommodate the entire arm, which makes the sleeve, when worn, taut and avoids the formation of pressure points. The strap is made of first and second segments which carry cooperating hook and loop fabrics for adjusting the length of the strap.

2 Claims, 3 Drawing Sheets

ARM SLING

This application is a division of and claims the benefit of U.S. application Ser. No. 09/129,197, filed Jul. 23, 1998, which is a continuation-in-part of U.S. application Ser. No. 08/665,271 filed Jun. 17, 1996 (now patent 5,792,083 dated Aug. 11, 1998), the disclosures of which are incorporated by reference.

RELATED APPLICATIONS

This application is a continuation-in-part application of Ser. No. 08/665,271, filed Nov. 17, 1996, for an ARM SLING, now U.S. Pat. No. 5,792,083.

BACKGROUND OF THE INVENTION

This invention relates to slings for optionally supporting a person's left or right arm.

Arm slings are extensively used whenever a person must protect and/or support his or her arm following an injury or sickness. A variety of arm slings is currently available on the market, and an even larger number of sling designs is known in the art as is exemplified, for example, by U.S. Pat. Nos. 2,594,809 and 4,285,337. Such arm slings have the common characteristic of forming a pouch into which the person's forearm can be placed so that his hand extends partially or fully from a front end of the pouch. A strap secured to the pouch adjacent its front and aft ends is slung over the person's shoulder so that the weight of the arm is supported by the pouch and the strap while the arm is kept in a protected manner close to the person's torso.

Typically, the pouches of prior art arm slings have a closed aft end and the strap, which is relatively wide to avoid undue pressure when it is draped over the person's shoulder and carries the weight of the arm, is secured, e.g. sewn, to an aft wall of the pouch which is oriented transversely to side panels of the pouch. The other end of the strap is suitably secured to the front end of the pouch, often with buckles, pins and the like, to facilitate the application of the arm sling and make the strap adjustable in length. The pouches and/or straps are frequently made of relatively stiff and strong material to render them more rigid, a feature which is at times enhanced by incorporating stiffening plates or the like into portions of the panel such as, for example, its lower base.

Prior art arm slings are fully capable of supporting the person's arm and frequently provide a degree of protection for the arm as well. By virtue of their construction they are, however, not longitudinally symmetrical and/or are not identical when worn on the left or the right arm. Further, they are relatively complex and, therefore, costly to produce. Moreover, when not in use, such slings are bulky and impractical to store in a small place and/or carry around; for example, in one's pocket for use when needed.

SUMMARY OF THE INVENTION

The present invention provides a simple, practical and lightweight arm sling which can be folded into a small package, not much bigger than a folded handkerchief, when not in use. The sling is longitudinally symmetric so that it can be applied identically to the left or the right arm. It can be made of inexpensive materials and requires minimal labor to produce so that it can be economically produced. Additionally, the sling is ideally adapted to be made of attractive materials such as fabrics having pleasant colors, designs and/or patterns, in distinction to the commonly utilitarian and drab-looking slings in current use.

Generally speaking, an arm sling constructed in accordance with the present invention can be made of two elongated panels of a soft fabric, such as a stretchable webbing, which are sewn together face-to-face along a seam which extends from a front end of the panels to the aft ends thereof. Alternatively, a single piece of such fabric is folded face-to-face to form the panels. In one embodiment of the invention, a single strap of the desired width has a first end which is disposed between opposing sides of the two panels adjacent their aft ends and, therefore, is parallel to the panels. A second end of the strap defines a front loop which extends parallel to the panels at the front ends thereof and is sewn thereto at three spaced-apart locations to define openings between each panel section and the overlying portion of the strap for anchoring the sling to the person's hand to prevent slippage during use. The entire strap is essentially parallel to the panels when the latter are placed flat-to-flat against each other; that is, the wide sides of both ends of the strap are arranged parallel to the panels and sewn to them so that, when folded, the entire strap and the panels are parallel. This renders the sling symmetric about a longitudinal center plate to render the sling truly reversible for left- or right-handed wear. In distinction to prior art slings, on which at least one strap end is non-parallel to the panels of the sling, this also draws the sling towards the patient's upper torso, which desirably stabilizes the arm in the sling.

In use, the panels are spread apart to define a trough or pouch into which the person's forearm can be placed. The strap is slung over the person's shoulder to support the arm in the pouch.

To prevent the sling from sliding back along the person's arm during use, any part of the person's hand, but preferably either the four fingers or the thumb or both, is extended through one or the other of the openings or loops defined by the portions of the strap which overlie the front ends of the panels.

Since the strap is parallel to the panels (when the panels are folded flat against each other) and a hand- or thumb-engaging opening or loop is provided at the front end on either side of the pouch, the sling is symmetrical about its longitudinal center plane and can be worn on the left arm or the right arm.

In a presently preferred embodiment of the invention, the panels which form the trough or pouch into which the arm is placed are made of soft, pliable and preferably stretchable material, such as the stretch material available on the market under the trademark Lycra. Such materials are mass-produced in many attractive colors, designs and patterns and they are available at reasonable costs. The material is soft so that it is readily assembled into a sling by cutting the panels and the straps from a sheet of such material and then sewing them together to form the arm sling of the present invention.

A presently preferred stretchable material for the panel is a cotton-spandex material (92% cotton, 8% spandex) which is marketed by Gilforth Guilfora Mills of North Carolina under the trade designation "No. 3035 Cotton Spandex French Terry" fabric.

Further, the length of the panels (in a direction parallel to the patient's arm) is selected so that the distance between the aft end of the trough and the loop engaged, for example, by the patient's four fingers (with the thumb located outside the loop) is less than the corresponding distance of the patient's arm measured from the elbow to the portion of the hand between the thumb and the four fingers, so that the sling must be stretched to apply it over the arm. Such stretching renders the sling taut, wrinkle-free and, therefore, attractive.

More importantly, by maintaining the material stretched and taut, the weight of the arm is more evenly distributed and the formation of pressure points, due, for example, to folds and creases which may form in loose materials, particularly relatively stiff fabric of which prior art slings were frequently made, is prevented. This renders the slings significantly more comfortable to wear and relieves weight on the neck muscles of the patient.

Still further, high-quality stretch fabrics, such as the above-referenced cotton-spandex material, permit sufficient longitudinal stretching of the sling to permit manufacturers to reduce the number of different-size arm slings that must be carried in inventory. This reduces both production and inventory costs. For example, the same-size sling made according to the invention can fit persons having a body weight between 90 and 250 lbs.

The versatility of the arm sling of the present invention is further enhanced by permitting longitudinal adjustment of the strap of the sling while maintaining its longitudinal symmetry so that the sling can be worn on either arm. In a preferred embodiment of the invention, the strap is made of first and second segments affixed, e.g. sewn, to the respective ends of the trough. One of the segments is made of two opposing parts, which can be spread apart into a V shape, and which receive, between them, a free end of the other strap segment. A Velcrol® type fastener system is appropriately incorporated in the opposing sides of the free strap end and the two-part strap so that the free strap ends can be longitudinally moved relative to each other for lengthening or shortening the strap. When the strap has the desired length, the spread-apart strap parts are pressed against the free end of the strap segment between them and the strap is ready for use.

Velcro® fastener systems or hook-loop connectors in the form of a fabric forming loops and a cooperating fabric forming hooks are commercially available under the trademarks Veltex® and Velcro®, respectively, from Velcro USA in Manchester, N.H.

Since the sling requires no hardware and is readily foldable, it can be folded into a small package only marginally larger than a folded handkerchief for storage and nonuse and can, for example, be carried in garment pockets.

Thus, the sling of the present invention is practical to use, economical to make, and can be sold at a relatively low price.

If desired, a simple, small buckle can be included in the strap to make its length adjustable.

DESCRIPTION OF THE PREFERRED EMBODIMENTS

Figure 1:
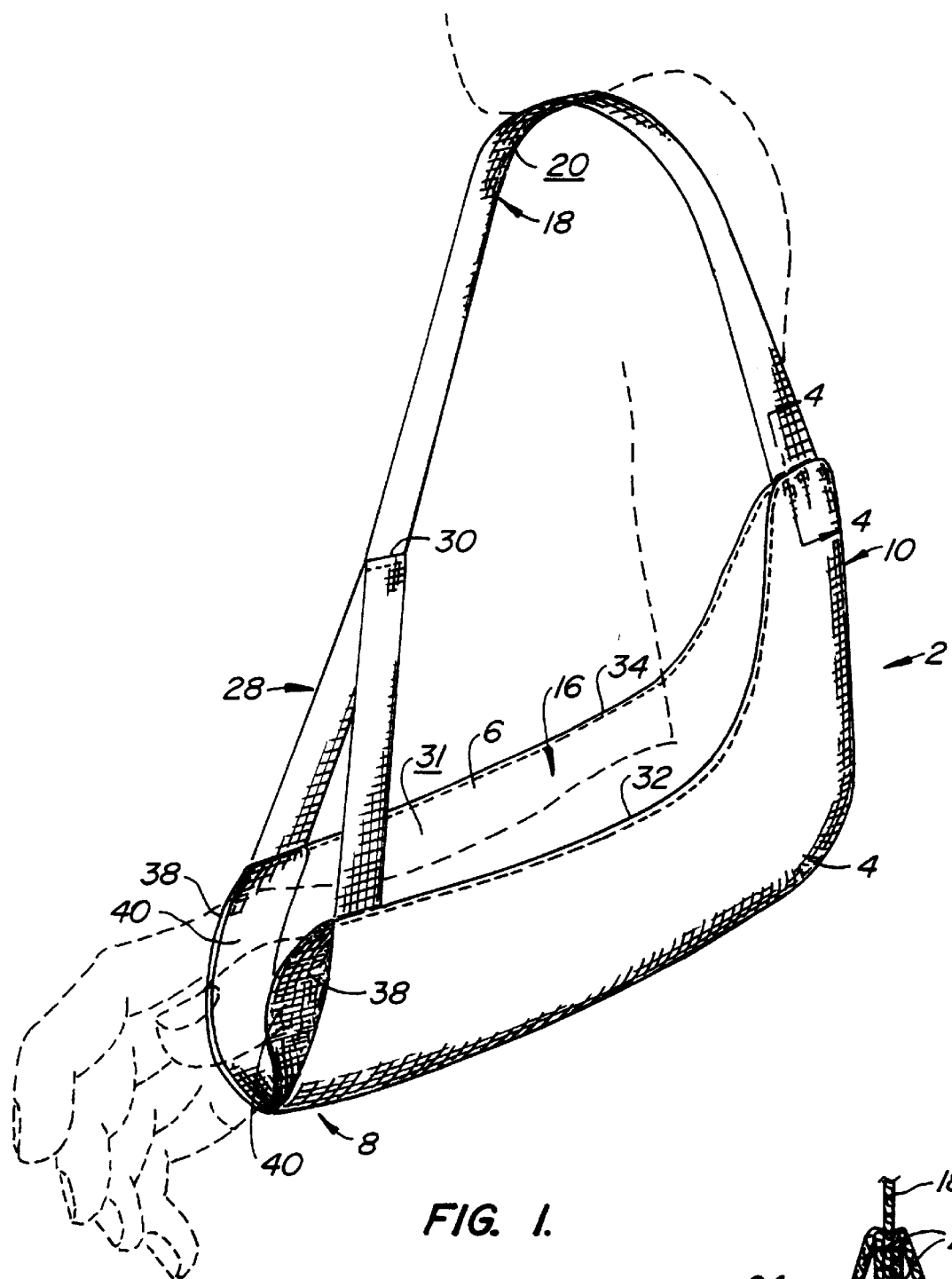
FIG. 1 is a perspective, front elevational view which shows the arm sling of the present invention supporting an arm (shown in phantom lines) of a person.
Figure 4:
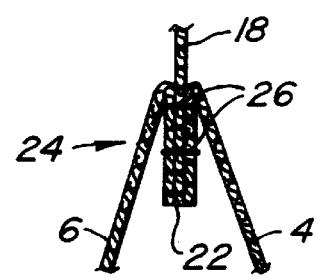
FIG. 4 is a partial, front elevational view in section and is taken on line 4—4 of FIG. 1.

Referring to the drawings, the arm sling 2 of the present invention is made of first and second, identically shaped, elongated panel sections 4, 6 which extend from a front end 8 of the sections to an aft end 10 thereof. Common lower and aft edges 12, 14 of the panel sections are stitched together so that the panel sections can be expanded, as is shown in FIG. 1, into an upwardly and forwardly open, and downwardly and rearwardly closed trough or pouch 16.

A relatively wide strap 18 has wide sides 20, an aft end 22 sandwiched between panel sections 4, 6 at an upper portion 24 of the aft end of the sections, and is secured thereto by stitching 26.

At the front end 8, strap 18 forms a loop 28 by doubling over a portion of the strap and attaching, e.g. sewing, the other end 30 of the strap to the remainder of the strap as is best seen in FIG. 1. A portion of the loop is placed against inner sides 31 of panel sections 4, 6 and attached, e.g. sewn, thereto adjacent upper edges 32, 34 of the panel sections to secure the strap and the panel sections to each other. The portion of the loop fitted against the sides of the panels which face each other is further secured to the panel sections at at least one additional location; for example, in the vicinity of lower panel edges 12. As a result, attachment member of loose strap parts 40 of the strap which overlie the inside surfaces of the panel sections can be lifted, as is illustrated in FIG. 1, to define openings 38, one each overlying each of the two panel sections.

Figures 2, 3:
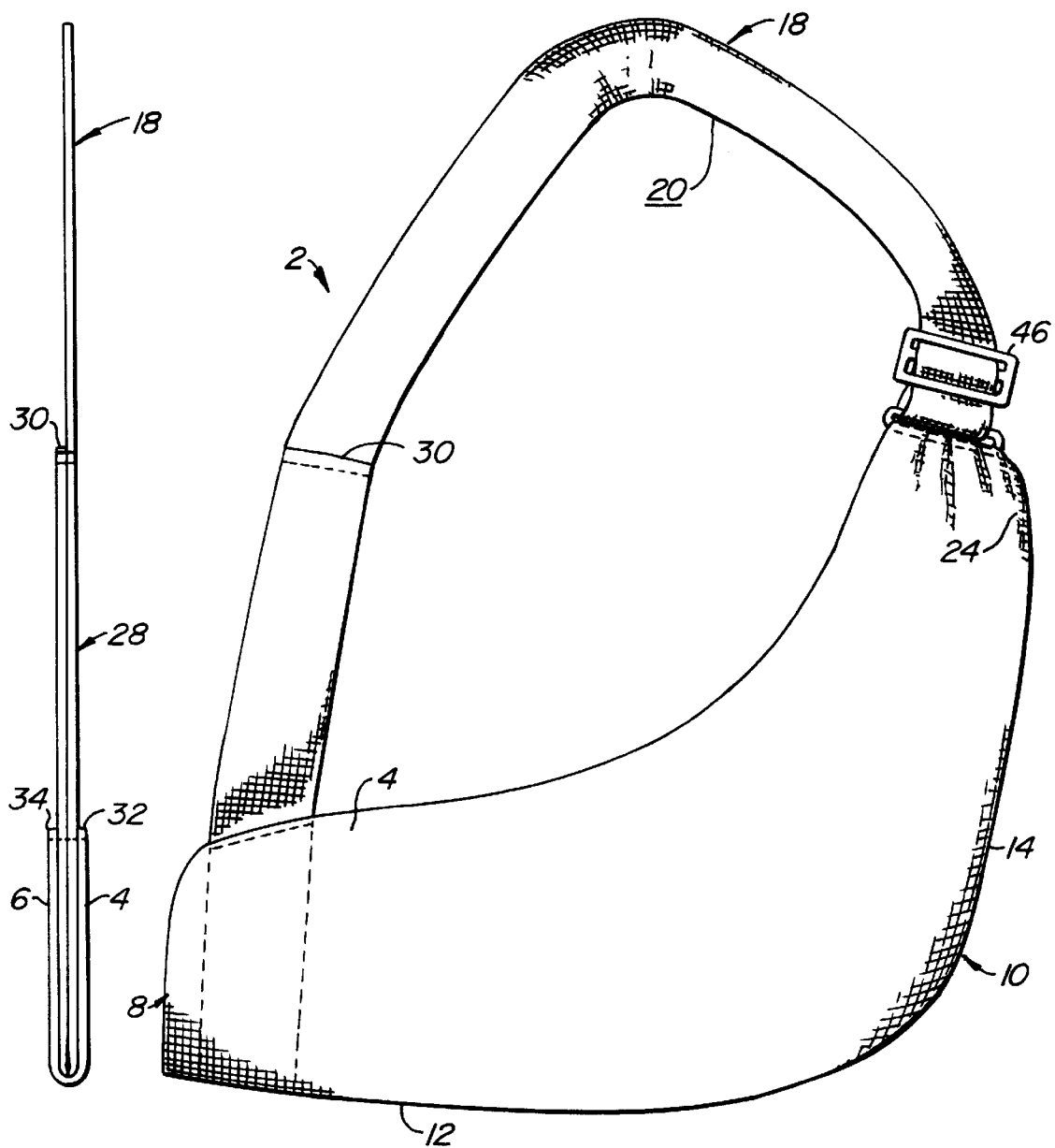
FIG. 2 is a side elevational view of a modified form of the arm sling in its collapsed position in which panels of the sling lie substantially flat face-to-face against each other.
FIG. 3 is a front elevational view of the folded sling shown in FIG. 1.

The arm sling is symmetrical about a vertical plane extending over the length of the panels and intersecting the lower edge 12 of the pouch (FIG. 2). As a result, when the arm is placed in the pouch of the sling and loop 28 is spread open as illustrated in FIG. 1 it can equally be used to support the right or the left arm.

The panel sections 4, 6 and strap 18 are constructed of the same, soft, pliable and preferable stretchable material, such as Lycra or cotton-spandex webbing or fabric.

Following the manufacture of arm sling 2, the panel sections are folded face-to-face flat against each other, as is illustrated in FIGS. 2 and 3, strap 18 is doubled over so that it overlies the panel sections, and the panel sections and the strap are then together folded into a small package for storage and shipment. The package is of such small size that it is readily placed in most garment pockets.

When the arm sling of the present invention is to be used, it is unfolded and the panel sections are spread apart into the configuration illustrated in FIG. 1 to form trough 16. The strap is slung over the person's shoulder and his or her forearm is placed into the trough as is illustrated in phantom lines in FIG. 1. When placing the arm into the trough, one or the other loose strap parts 40 is lifted to form opening 38 and the person's thumb is extended through the opening, as is also illustrated in FIG. 1. Arm sling 2 now supports the weight of the arm from the person's shoulder and the thumb engages strap part 40 and anchors the sling to the person's hand so that the sling cannot slide backwardly along the person's arm during use.

Referring now to FIG. 2, in one embodiment of the invention the length of strap 18 is adjustable. The strap is secured to the front end 8 of the sling as previously described. A buckle 46 of conventional construction is carried by the strap in the vicinity of its aft end. The free end portion of the strap is extended through the buckle and appropriately attached thereto, by means of a friction fit or a clasp (not shown) after the desired overall strap length has been set. In all other respects, an arm sling which includes a strap length adjustment buckle is constructed and used as described above.

Figures 5, 6, 7:
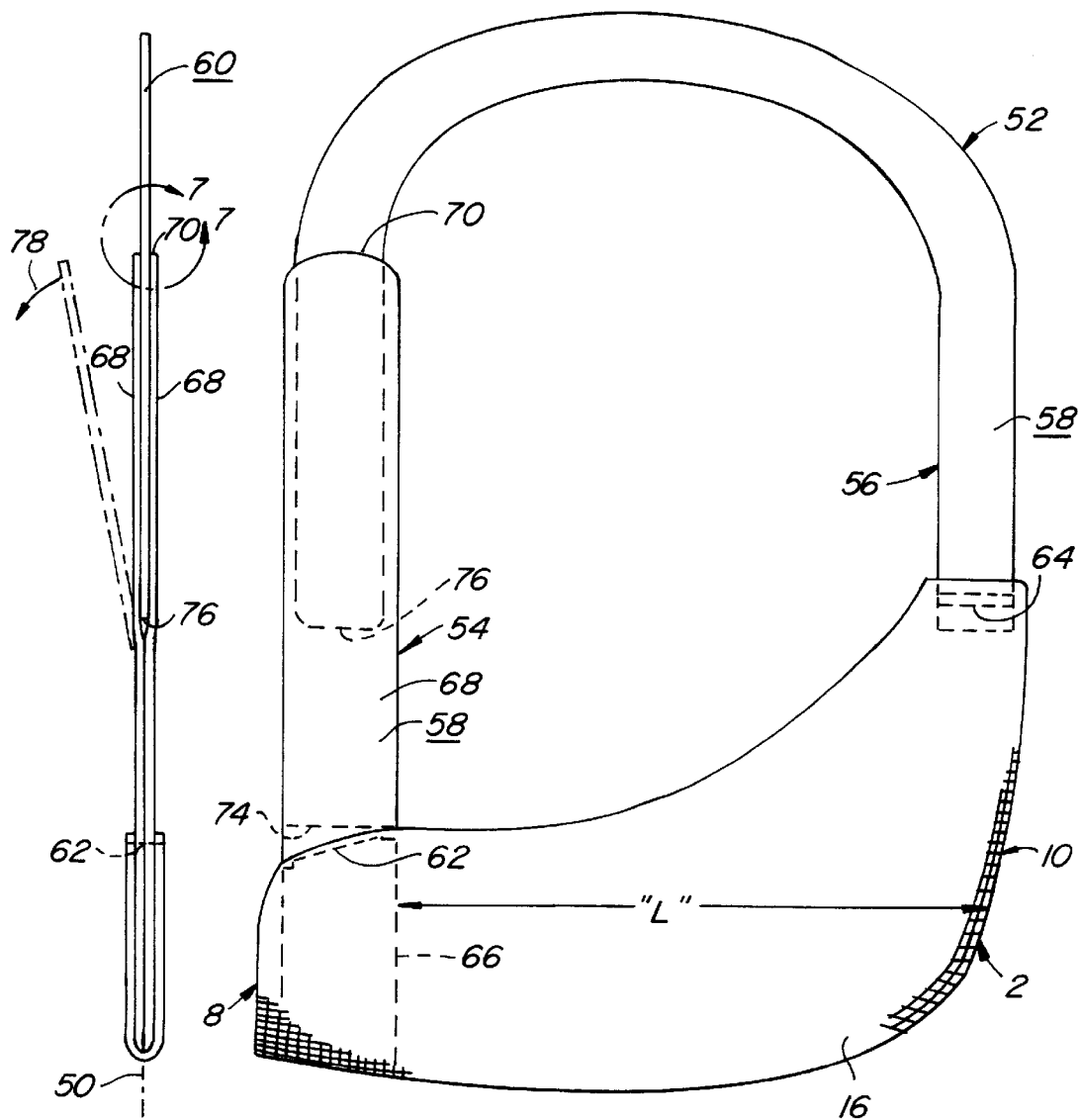
FIG. 5 is a side elevational view similar to FIG. 2 and illustrates a presently preferred embodiment of the invention.
FIG. 6 is a front elevational view of the folded sling shown in FIG. 5.
FIG. 7 is a fragmentary, enlarged, side elevational view of the portion of FIG. 3 denoted by line 7—7.

Referring now to FIGS. 5–7, another embodiment of the present invention also has an arm sling 2 which forms an upwardly and forwardly open, and downwardly and rearwardly closed, trough or pouch 16 that has a forward end 8 and an aft end 10. The pouch is preferably constructed of a single piece of the above-referenced cotton-spandex fabric that is folded face-to-face so that each half of the fabric is symmetrical about a longitudinal, upright center plane 50 that extends over the length of the pouch. Aft end 10 is sewn closed and a carrying strap 52 made of first and second strap segments 54, 56 and having sets of opposing, spaced-apart wide sides 58 and narrow sides 60, respectively, is affixed, e.g. sewn along stitching lines 62, 64, to the trough by arranging the wide sides of the strap ends between the trough panels so that they are parallel. Additional lengths of strap material 66 (which may be the same as or different from strap 52) are attached, e.g. sewn, adjacent forward end 8 to the sides of the trough panels facing each other so that a loop (not separately shown in FIGS. 5–7) is formed between each strap length and the associated panel similar to the loops shown in FIG. 1 (reference numeral 38). The loops are preferably sized so that the four fingers of a hand can extend through them while the associated thumb is disposed outside that loop. When the fingers are inserted through the loop, with or without extending the thumb through the other loop, relative movement of the sling in an aft direction is limited by the engagement of the portion of the hand between the index finger and the thumb and the associated loop. Conversely, when the sling is worn, the hand will not hang loosely from the open front end of the sling.

First strap segment 54 is made of two strap parts 68 which are of equal length and terminate in first strap ends 70. Strips of hook fabric material 72 (sold under the trademark Velcro®) are secured to sides of the strap parts facing each other, for example by stitching, and they extend from the free ends of the strap parts to adjacent the pouch as is indicated by phantom line 74 in FIG. 5.

Second strap segment 56 has a free end 76 which is disposed between the layers of hook material on the inside of strap parts 68. The entire second strap segment is preferably constructed of a loop fabric (such as the fabric sold under the trademark Veltex®) so that any portion of the strap can be engaged by the hook fabric on strap parts 68. By pressing the strap parts together, the hook material engages the loop material in a well-known manner to form a releasable connection between them. To release the connection, the strap parts 68 are pulled apart (as schematically illustrated in FIG. 6 by arrow 78), thereby releasing the connection between the two strap segments. The length of strap 52 can be adjusted by extending a greater or lesser length of the second strap segment between the opposing strap parts 68. In addition, the length of the sling can be significantly shortened by cutting off a portion of the second strap segment. This is desirable, for example, for using the arm sling to hold an arm in a relatively elevated position against the patient's upper torso.

Dimensionally, trough 16 is formed so that its relaxed length "L" from strap material 66, which forms the hand-engaging loops of the sling, to aft end 10 of the sling is less than a corresponding distance from between the thumb and index finger of a patient's hand to the elbow end of the arm that is to be placed into the sling. As a result, the sling becomes longitudinally stretched or elongated when it is applied over the patient's arm, which renders the sling taut and, during use, prevents the formation of pressure points.

What is claimed is:

1. A method for supporting an arm comprising the steps of folding a panel of a stretchable material so that it forms an arm-receiving trough having an open front end and a closed aft end, suspending the trough with a strap from a body portion of a patient, placing the arm in the trough, abutting an elbow end of the arm against the closed aft end of the trough, placing the front end of the trough adjacent the hand of the patient, longitudinally elongating the panel by stretching the material, and attaching a portion of the panel in a vicinity of the front end of the trough to the hand while the panel is elongated so that the panel is taut and supports the arm substantially free of pressure points.

2. A method of comfortably supporting a patient's arm in a sling forming a trough into which the patient's arm can be placed comprising constructing the sling of a stretchable material, providing an attachment point for a portion of an elbow and a separate attachment member for a portion of a hand of the arm on the sling so that, prior to applying the sling to the arm, a distance between the attachment point and attachment member is less than a distance between the portions at the elbow and the hand to be engaged by the attachment point and attachment member, applying the sling to the arm and hand, engaging a digit with the attachment member to anchor the sling to the hand by stretching the sling until the distance between the attachment point and attachment member of the sling has been elongated to correspond to the distance between the patient's elbow and hand, and thereafter supporting the arm in the sling.

* * * * *